United States Patent
Wessman et al.

(10) Patent No.: US 7,555,349 B2
(45) Date of Patent: Jun. 30, 2009

(54) LEAD BODY AND METHOD OF LEAD BODY CONSTRUCTION

(75) Inventors: Bradley J. Wessman, Wilmington, NC (US); Peter J. Pohndorf, Stillwater, MN (US); Mark Gerald Schrom, Hugo, MN (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 654 days.

(21) Appl. No.: 11/329,442

(22) Filed: Jan. 11, 2006

(65) Prior Publication Data

US 2006/0111768 A1    May 25, 2006

Related U.S. Application Data

(63) Continuation-in-part of application No. 09/821,919, filed on Mar. 30, 2001, now Pat. No. 7,149,585, and a continuation-in-part of application No. 11/074,572, filed on Mar. 8, 2005, which is a continuation of application No. 09/822,728, filed on Mar. 30, 2001, now Pat. No. 6,952,616, which is a continuation-in-part of application No. 09/670,062, filed on Sep. 26, 2000, now Pat. No. 7,039,470.

(51) Int. Cl.
A61N 1/05 (2006.01)

(52) U.S. Cl. ....................................... 607/116
(58) Field of Classification Search .................. 607/116
See application file for complete search history.

(56) References Cited

U.S. PATENT DOCUMENTS

| | | | |
|---|---|---|---|
| 3,378,673 A | 4/1968 | Hopper | |
| 3,572,344 A | 3/1971 | Bolduc | |
| 3,760,812 A | 9/1973 | Timm et al. | |
| 4,280,511 A | 7/1981 | O'Neill | |
| 4,355,646 A | 10/1982 | Kallock et al. | |
| 4,381,014 A | 4/1983 | Sandstrom et al. | |
| 4,432,377 A | 2/1984 | Dickhudt | |
| 4,437,474 A | 3/1984 | Peers-Trevarton | |
| 4,444,195 A | 4/1984 | Gold | |
| 4,484,586 A | 11/1984 | McMickle et al. | |
| 4,559,951 A | 12/1985 | Dahl et al. | |
| 4,566,467 A | 1/1986 | Dehaan | |
| 4,590,950 A | 5/1986 | Iwaszkiewicz et al. | |
| 4,592,372 A | 6/1986 | Beranek | |
| 4,614,395 A | 9/1986 | Peers-Trevarton | |
| 4,630,611 A | 12/1986 | King | |
| 4,706,682 A | 11/1987 | Stypulkowski et al. | |
| 4,764,324 A | 8/1988 | Burnham | |
| 4,848,352 A | 7/1989 | Pohndorf et al. | |

(Continued)

FOREIGN PATENT DOCUMENTS

EP    0 647 435    4/1995

*Primary Examiner*—Carl H. Layno
*Assistant Examiner*—Jon-Eric C. Morales
(74) *Attorney, Agent, or Firm*—Christopher S. L. Crawford; Peter Lando; Melissa Acosta

(57) ABSTRACT

In one embodiment, a neurostimulation lead, comprises: a lead body, the lead body comprising an inner insulator, an outer insulator positioned around the inner insulator, wherein the outer insulator and the inner insulator are fused together; at least one conductor that is wound between the inner insulator and the outer insulator; and at least one electrode that is electrically coupled to the at least one conductor.

10 Claims, 4 Drawing Sheets

U.S. PATENT DOCUMENTS

| | | |
|---|---|---|
| 4,890,623 A | 1/1990 | Cook et al. |
| 4,934,049 A | 6/1990 | Kiekhafer et al. |
| 4,944,088 A | 7/1990 | Doan et al. |
| 4,945,342 A | 7/1990 | Steinemann |
| 5,016,646 A | 5/1991 | Gotthardt et al. |
| 5,040,544 A | 8/1991 | Lessar et al. |
| 5,118,400 A | 6/1992 | Wollam |
| 5,178,957 A | 1/1993 | Kolpe et al. |
| 5,231,996 A | 8/1993 | Brady et al. |
| 5,251,643 A | 10/1993 | Osypka |
| 5,324,322 A | 6/1994 | Grill, Jr. et al. |
| 5,350,404 A | 9/1994 | Adams et al. |
| 5,374,285 A | 12/1994 | Vaiani et al. |
| 5,417,208 A | 5/1995 | Winkler |
| 5,431,681 A | 7/1995 | Helland |
| 5,433,742 A | 7/1995 | Willis |
| 5,458,629 A | 10/1995 | Baudino et al. |
| 5,476,495 A | 12/1995 | Kordis et al. |
| 5,555,618 A | 9/1996 | Winkler |
| 5,582,609 A | 12/1996 | Swanson et al. |
| 5,609,622 A | 3/1997 | Soukup et al. |
| 5,712,462 A | 1/1998 | Berkowitz et al. |
| 5,746,616 A | 5/1998 | Mar |
| 5,762,631 A | 6/1998 | Klein |
| 5,772,693 A | 6/1998 | Brownlee |
| 5,788,692 A | 8/1998 | Campbell et al. |
| 5,796,044 A | 8/1998 | Cobian et al. |
| RE35,924 E | 10/1998 | Winkler |
| 5,824,026 A | 10/1998 | Diaz |
| 5,840,031 A | 11/1998 | Crowley |
| 5,928,277 A | 7/1999 | Laske et al. |
| 5,935,159 A | 8/1999 | Cross, Jr. et al. |
| 5,951,539 A | 9/1999 | Nita et al. |
| 5,957,910 A | 9/1999 | Holden, II et al. |
| 6,018,684 A | 1/2000 | Bartig et al. |
| 6,143,013 A | 11/2000 | Samson et al. |
| 6,151,520 A | 11/2000 | Combs |
| 6,208,881 B1 | 3/2001 | Champeau |
| 6,216,045 B1 | 4/2001 | Black et al. |
| 6,249,708 B1 | 6/2001 | Nelson et al. |
| 6,253,111 B1 | 6/2001 | Carner |
| 6,295,476 B1 | 9/2001 | Schaenzer |
| 6,324,415 B1 | 11/2001 | Spehr et al. |
| 6,400,992 B1 | 6/2002 | Borgersen et al. |
| 6,434,430 B2 | 8/2002 | Borgersen et al. |
| 6,451,005 B1 | 9/2002 | Saitou et al. |
| 6,477,427 B1 | 11/2002 | Stolz et al. |
| 6,701,191 B2 | 3/2004 | Schell |

LEAD BODY AND METHOD OF LEAD BODY CONSTRUCTION

RELATED APPLICATIONS

The present application claims the benefit under 35 U.S.C. § 120 of, and is a continuation in part of, the following, commonly assigned applications: U.S. patent application Ser. No. 09/821,919, filed Mar. 30, 2001, now U.S. Pat. No. 7,149,585 entitled "Lead Body and Method of Lead Body Construction;" and U.S. patent application Ser. No. 11/074,572, filed Mar. 8, 2005, entitled "Method of Forming a Lead" which is a continuation of U.S. patent application Ser. No. 09/822,728, filed Mar. 30, 2001, entitled ~Medical Lead and Method For Electrode Attachment" (now issued as U.S. Pat. No. 6,952,616) which is a continuation in part of U.S. patent application Ser. No. 09/670,062, filed Sep. 26, 2000, now U.S. Pat. No. 7,039,470 entitled "Medical Lead and Method For Medical Lead Manufacture," all of which are incorporated herein by reference.

TECHNICAL FIELD

The present application relates to medical devices and more particularly, to a lead body for a medical lead and a method for constructing a lead body.

BACKGROUND

A variety of medical electrode catheters are available today for the diagnosis and treatment of various disorders of the cardiovascular and neurological systems. These electrode catheters can be used to sense electrical activity within the body and to deliver different forms of energy to stimulate, ablate, cauterize or pace. Examples of medical catheters using electrodes include permanent and temporary cardiac pacing leads, electrophysiologic (EP) catheters, electrocautery probes and spinal stimulation catheters. Generally, for all applications, a reduced diameter lead is desired to limit the negative steric effects of lead implantation. Therefore, a need exists for a reduced diameter lead to reduce the negative effects of lead implantation.

In addition, lead size can prevent access to certain tissues and structures. In the case of neurostimulation, spinal cord stimulation may have a limited effectiveness for certain pain conditions. In many cases where spinal cord stimulation is inadequate, spinal or peripheral nerves must be specifically stimulated to provide pain relief. However, access to spinal and peripheral nerves is limited because of the limited space for lead placement within the intervertebral foranin. Therefore, with existing technology, access to certain nerves is best accomplished using a laminectomy procedure. In a laminectomy procedure, a portion of a vertebrae's lamina is surgically removed to allow placement of an electrode adjacent to the target nerve. The surgery frequently results in significant scarring and patient discomfort. Therefore, a need exists for a method to manufacture of a reduced diameter body lead to provide improve access for nerve stimulation.

Procedurally, spinal or peripheral nerve stimulation is more challenging than spinal chord stimulation. The spinal and peripheral nerves branch off of the spinal chord through the transverse foramen of the vertebrae. Spinal and peripheral nerve stimulation is necessary when a region of the body is affected that cannot be effectively stimulated via the spinal cord. To stimulate these nerves, a lead is inserted through the epidural space along the spinal chord and then turned laterally outward to track the branching nerves. Tracking these nerves requires a lead having a significantly smaller diameter than conventional stimulation leads. Further, in deep brain stimulation, a reduced diameter lead may provide for less traumatic placement of electrodes as well as more precise electrical stimulation by allowing electrode placement directly adjacent to remote target locations within the brain. Therefore, a need exists for the manufacture of a reduced diameter lead to improve access in neurological applications.

In cardiac applications, a reduced diameter leads may provide access to locations within the heart and veins that would not otherwise accessible. In addition, smaller leads allow more efficient valve function than their standard diameter counterparts when the lead passes through the valves in the heart. Further, smaller leads allow access to smaller veins without compromising blood flow. Thus, a need exists for a reduced diameter lead configured for cardiac pacing.

Prior methods for the manufacture of lead bodies either wound heated conductors into insulating material and then passed the lead bodies through a smoothing dye or wound conductors over an inner insulator and then extruded an outer insulator over the conductors. These methods do not allow for the precise control of variables such as conductor positioning and pitch during manufacture because the methods may permit the conductors to float during manufacture. Imprecise positioning can result in electrical contact between adjacent conductors resulting in the particular lead body having to be discarded. Therefore, a need exists for a method that allows for more precise control and tighter tolerances during manufacture. Further, these methods have a tendency to destroy outer coverings that may be present on the wires during manufacture. Therefore, a need also exists for a method of forming a lead body that does not destroy the integrity of coverings, such as for example insulators, during manufacture.

The present application meets the above needs and provides other improvements and advantages that will be recognized by those skilled in the art upon review of the following description and drawings.

SUMMARY

A lead body in accordance with one embodiment includes an inner insulator, an outer insulator and at least one conductor. The conductor is wound between the inner insulator and the outer insulator and the outer insulator and the inner insulator are fused together. When the lead body includes a plurality of conductors, the inner insulator may be fused to the outer insulator to electrically isolate the conductors from one another. The lead body may further include a lead body a lumen extending through the inner insulator along the longitudinal axis of the lead body. One or more insulating spacers may also be provided between the inner and outer insulator to space and/or electrically insulate the conductors. The least one insulating spacers may be fused to either or both of the inner insulator and the outer insulator.

A lead body in accordance with one embodiment may be manufactured by positioning at least one conductor between an outer and an inner insulator and fusing the outer and the inner insulators to one another. In one embodiment, the inner insulator is disposed about a mandrel intermediate a first end and a second end of the mandrel. The first end and the second end of the mandrel are typically exposed. A first end of the at least one conductor is secured to the first end of the mandrel. The at least one conductor is then spirally wound around the inner insulating material and the second end of the conductor is secured to the second end of the mandrel. One or more insulating spacers may be provided and spirally wound between the conductors. An outer insulating material is then disposed around the wound conductor coextensive with the inner insulating material. The inner and outer insulators are then fused by heating. The fusing may be facilitated by disposing shrink-wrap tubing over the outer insulating material and heating the shrink-wrap, the outer insulating material and the inner insulating material. The heating shrinks the shrink-wrap tubing and forces the outer insulating material to contact the inner insulating material. The shrink-wrap may be removed after the layers have been fused. The fusing may also be facilitated by disposing tubing over the outer insulating material, sealing a first end of the tubing, applying a partial vacuum to a second end of the tubing, and heating the tubing. The vacuum draws the inner and outer insulators into contact with one another and the heating fuses the outer insulating material to the inner insulating material. The mandrel may be removed from the lead body to form a lumen or may remain within the lead body.

DETAILED DESCRIPTION

Figure 1A:
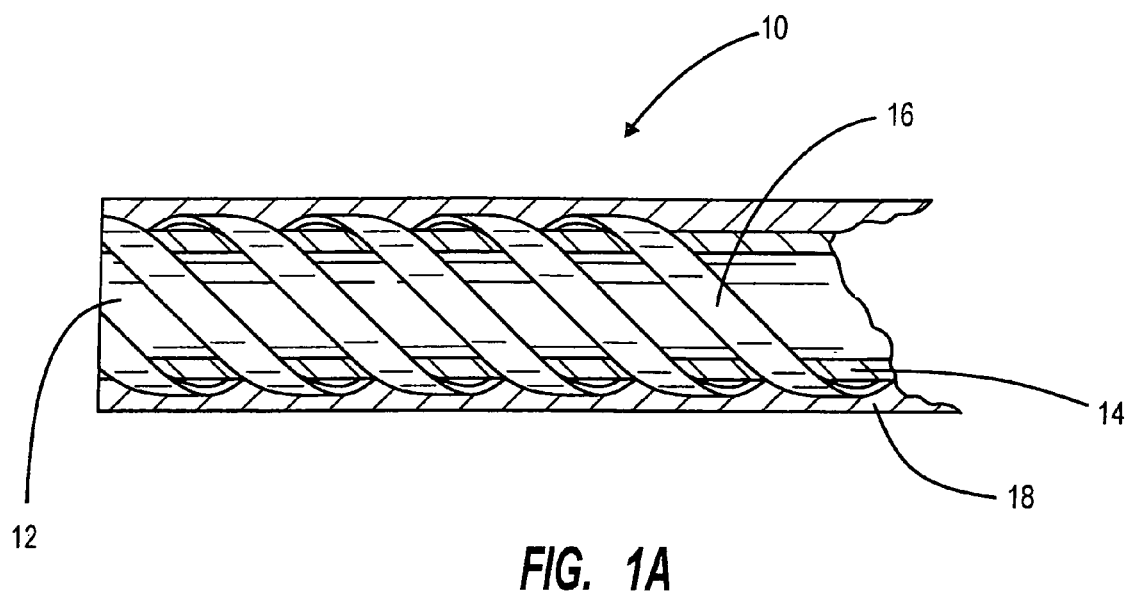
FIG. 1A illustrates a longitudinal cross-section of an embodiment of a lead body in accordance with one embodiment.

The present application provides a novel method for the manufacture of lead body and provides a novel lead body for use in a variety of medical applications. The application describes particular embodiments described below for exemplary purposes only, those skilled in the art will understand how to apply the disclosed embodiments to a variety of lead bodies. Therefore, the appended claims are not intended to be limited to any specific example or embodiment described in this patent. Further, in the drawings described below, reference numerals are generally repeated where identical elements appear in more than one figure.

Figure 1B:
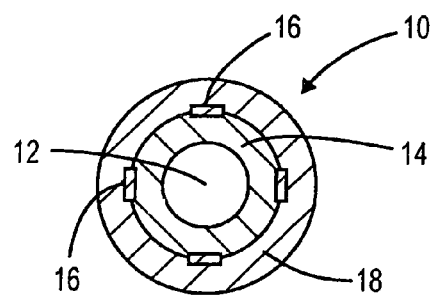
FIG. 1B illustrates a transverse cross-section of the embodiment of a lead body as shown in FIG. 1A.

A lead body in accordance with one embodiment is illustrated in FIGS. 1A and 1B. Lead body 10 includes a lumen 12, an inner insulator 14, at least one conductor 16 and an outer insulator 18. Conductor 16 may be in the form of a round wire, a square wire, a cable, or other elongated form. Conductors 16 are shown as ribbon wire having a rectangular cross-section for exemplary purposes only. Further, conductors 16 may be solid wires, a drawn-filled-tube or other configuration of conductor that will be recognized by those skilled in the art. Conductors 16 are typically composed of stainless steel, MP35N, platinum, gold, silver, copper, vanadium or other metal. Further, conductors 16 may include a conductor insulator or other covering disposed about the individual conductors. Typically, the conductor insulator is a polymeric or silicone based material. Conductors 16 typically extend from a first end to a second end of the lead body. Conductors 16 are typically wound about the lumen and are insulated from the external environment by outer insulator 18 and from the lumen by inner insulator 14. Inner insulator 14 and outer insulator 18 are fused together during manufacture. The fused inner insulator 14 and outer insulator 18 can electrically isolate individual conductors 16 from one another. Inner insulator 16 and outer insulator 18 may be the same or different materials. The inner insulator 16 and outer insulator 18 are typically made from an insulating material such as polyurethane or silicone rubber. To facilitate fusing during manufacture, the materials of inner insulator 16 and outer insulator 18 have a similar melting point. The similarity between the melting points of inner insulator 16 and outer insulator 18 permits fusing of the insulators after softening the materials using heat without a substantial disruption in their shape from melting. The materials selected for insulators 16 and 18 may have disparate durometers to alter the flex characteristics for particular applications. Further, an insulating spacer 21, shown in FIG. 5, may be wound between the individual conductors during manufacture to further electrically isolate adjacent conductors. Insulating spacer 21 typically being formed of a material that will fuse to inner insulator 16 and outer layer 18 during manufacture.

Figure 2:
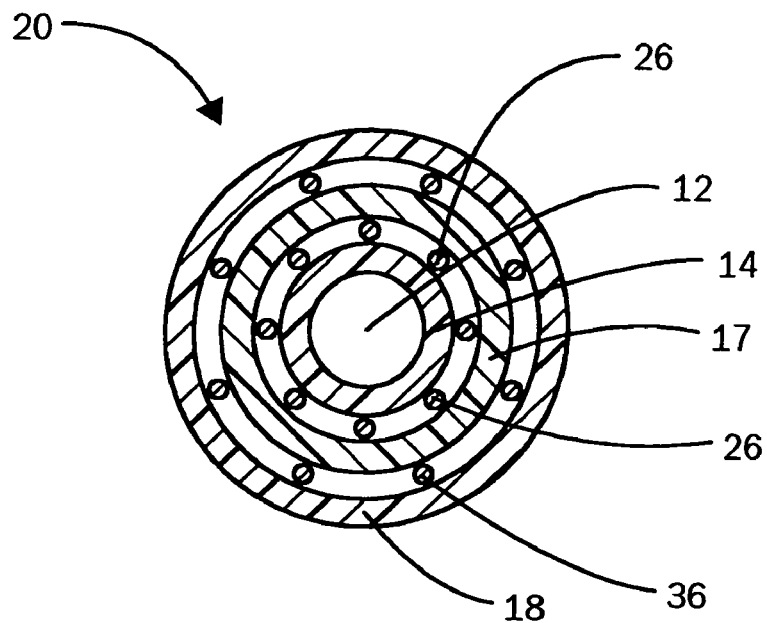
FIG. 2 illustrates a transverse cross-section of another embodiment of a lead body in accordance with one embodiment.
Figure 5:
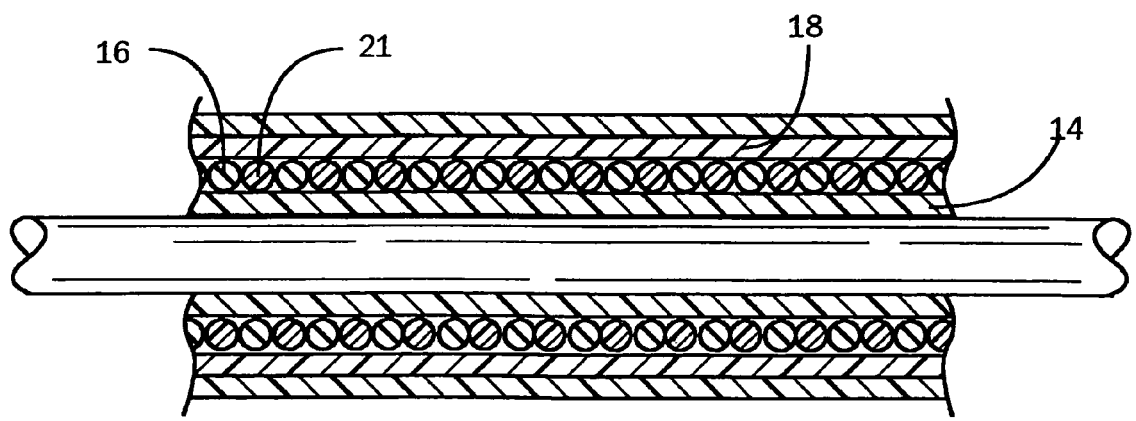
FIG. 5 illustrates a lead body including an insulating spacer.

FIG. 2 illustrates a transverse cross-section of another embodiment of a lead in accordance with one embodiment. Lead body 20, as shown in FIG. 2, includes a lumen 12, an inner insulator 14, at least one inner conductor 26, an intermediate insulator 17, at least one outer conductor 36 and an outer insulator 18. Inner conductors 26 and outer conductors 36 typically extend from a proximal end of the lead body to a distal end of the lead body and may be wound in the same or opposite directions within the lead body. Inner conductors 26 are typically wound around inner insulator 14 and are insulated from the outer conductors 36 by intermediate insulator 17. Outer insulator 18 electrically isolates the conductors from the exterior environment and inner insulator 16 electrically isolates the conductors from the lumen. Inner insulator 16, intermediate insulator 17 and outer insulator 18 are fused together and function to electrically isolate the conductors from one another. In addition, lead body 10 may include an insulating spacer 20, as shown in FIG. 5, wound between either or both of inner conductors 26 and outer conductors 36. An insulating spacer 21 between inner conductors 26 can be fused between inner insulator 16 and intermediate layer 17 to electrically isolate adjacent conductors. An insulating spacer 21 between outer conductors 36 can be fused between intermediate layer 17 and outer insulator 18 to electrically isolate adjacent conductors. Additional insulating layers and additional layers of conductors may be provided as required by particular applications to alter the flexibility, torquability and/or diameter of lead body 20. When providing multiple layers of conductors only one layer of conductors need be conductive, the additional layers may be provided in a manner to confer particular physical properties to the lead body, such as torqueability. The non-conductive materials which can be used may include nylon, polytetrafluoroethylene (PTFE), and other non-conductive materials that may be formed into filaments and wound.

Figure 3:
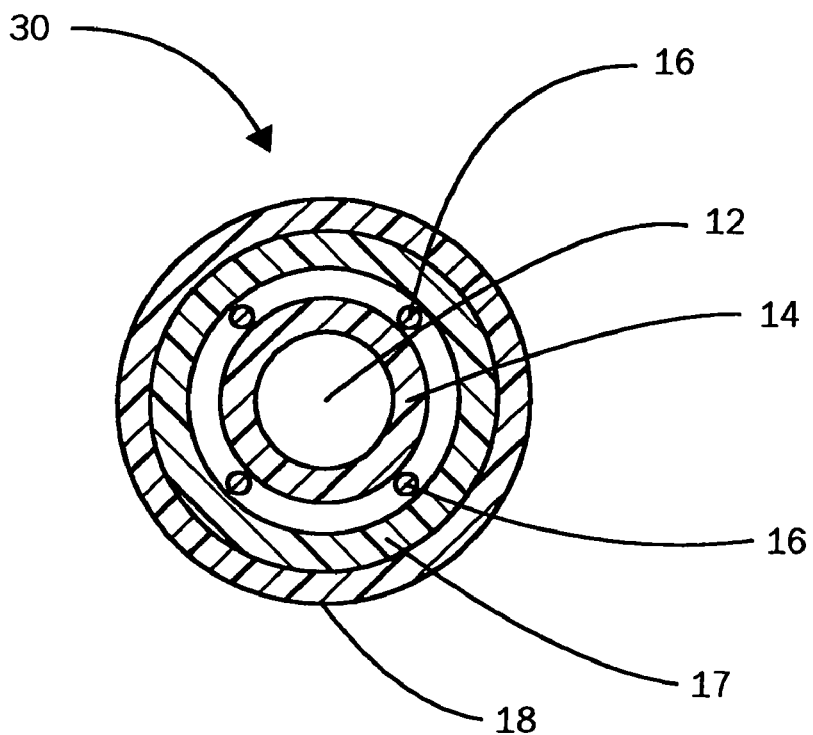
FIG. 3 illustrates a transverse cross-section of yet another embodiment of a lead body in accordance with one embodiment.

FIG. 3 illustrates a transverse cross-section of yet another embodiment of a lead in accordance with one embodiment. Lead body 30, as shown in FIG. 3, includes a lumen 12, an inner insulator 14, at least one conductor 16, an intermediate insulator 17, and an outer insulator 18. Conductors 16 typically extend from a first end of to a second end of lead body 30. Conductors 16 are typically wound around inner insulator 14 and are insulated by intermediate insulator 17. Outer insulator 18 may extend for the entire length of lead body 30 or for only a portion of the length of lead body 30. Outer insulator 18 may function to alter either or both of the flex characteristics of lead body 30 and the diameter along the length of lead body 30 as may be required in certain applications. Inner insulator 16, intermediate insulator 17 and outer insulator 18 are fused together during manufacture. In addition, lead body 30 may include an insulating spacer 21, as shown in FIG. 5, wound between inner conductors 26. An insulating spacer 20 between conductors 16 can be fused between inner insulator 16 and intermediate layer 17 to electrically isolate adjacent conductors 16. An insulating spacer 21 between outer conductors 36 can be fused between intermediate layer 17 and outer insulator 18 to electrically isolate adjacent conductors. Additional insulating layers may be provided as required by particular applications to alter the flexibility, torquability and/or diameter of lead body 30.

Figure 4A:
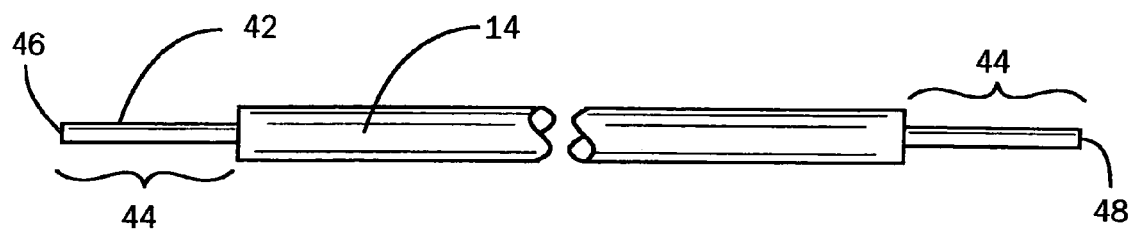
FIG. 4A illustrates a perspective view of a mandrel covered with the inner insulator.
Figure 4B:
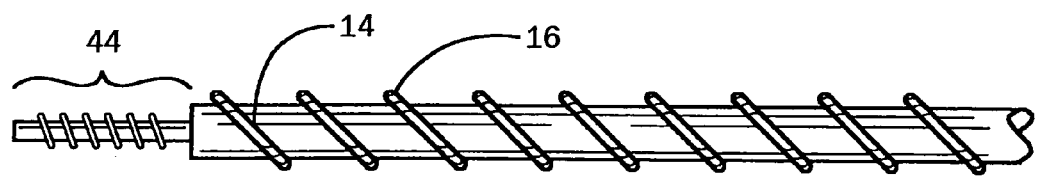
FIG. 4B illustrates a perspective view of a mandrel covered with the inner insulator having a conductor wound over the inner insulator.
Figure 4C:
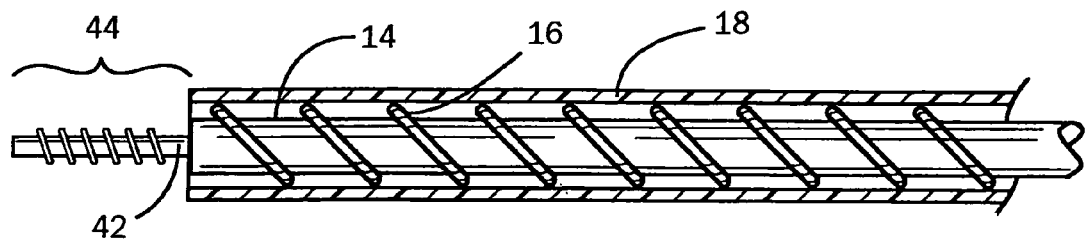
FIG. 4C illustrates a partial cross-section of an embodiment prior to fusing the outer insulator to the inner insulator.

A lead body in accordance with one embodiment may be manufactured using a process outlined in FIGS. 4A to 4C. FIG. 4A illustrates an inner insulator 14 is disposed about a mandrel 42. Inner insulator 16 may be extruded over the mandrel or may otherwise be deposited about the mandrel as will be recognized by those skilled in the art. For manufacture of reduced diameter leads, mandrel 42 may, for example, be a wire having a diameter of around 0.013 inch. Typically, the mandrel's diameter is selected as appropriate for the end use of the particular lead body. Further, mandrel 42 may have a variety of cross-sectional shapes as required by particular applications. FIG. 4A further illustrates a pair of attachment regions 44 provided along mandrel 42. Attachment regions 44 provide locations for attachment of conductors 16, shown in FIG. 4B, during manufacture. Attachment regions 44 are typically exposed portions of mandrel 42 without any inner insulator 14 and are typically provided at both a first end 46 and a second end 48 of mandrel 42. Typically, a length of mandrel 42 and inner insulator 14 are cut from a spool of insulator covered mandrel after a continuous extrusion process prior to forming attachment region 44, although the insulator covered mandrel may be constructed in any of a variety of methods that will be recognized by those skilled in the art. The length of mandrel 42 and inner insulator 14 cut from the spool will depend on the particular application for the lead body. Alternatively, mandrel 42 and inner insulator 14 may be prefabricated in the desired length. Typically, attachment region 44 is formed by stripping the insulator 16 from mandrel 42 after extrusion, although attachment region 44 may be formed during the deposition of inner insulator 14 on mandrel 42. Attachment region 44 provides a region of reduced diameter to which the first and second ends of conductors 16 will be attached to prevent unwinding during manufacture. FIG. 4C illustrates the attachment of the conductors. A first end of conductors 16 is secured to an attachment region 44 at first end 46 of mandrel 42. Conductors 16 may be secured by winding around attachment region 44, by adhesives, by shrink tubing, by welding or by other methods that will be recognized by those skilled in the art. FIGS. 4B and 4C illustrate conductors 16 secured by winding for exemplary purposes. The method of securing is typically chosen so that the outside diameter of the secured conductor ends does not exceed the outside diameter of conductors 16 wound over insulator 14. Maintaining an equal or smaller diameter for the secured ends of conductors 16 permits the passing of a length of outer insulator 18 in the form of a tube over attachment region 44 for positioning over wound conductors 16 and inner insulator 14 as illustrated in FIG. 4C. Again referring to FIG. 4B, once the proximal end of the conductor are secured, a desired number of conductors 16 are wound over inner insulator 14 at a desired pitch and tension. Once the winding has reached second end 48 of mandrel 42, a second end of conductors 16 is secured to a second attachment region 44 at second end 48 to prevent conductors from unwinding during subsequent steps of manufacture. In addition to conductors 16, an insulating spacer 21, shown in FIG. 5, may be separately or simultaneously wound between conductors. Insulating spacer 21 can function to maintain the spacing of the wires during manufacture and to further insulate the individual conductors in the finished lead body. Outer insulator 18 is then applied over conductors 16. Typically, outer insulator 18 is provided in the form of a tube, although the material may be provided as a sheet and wrapped around the conductors. Additional layers of conductors and insulators may also be provided as outlined above. Once outer insulator 18 has been provided over conductors 16, outer insulator 18 is fused to inner insulator 14 by heating the lead body or alternatively, outer insulator 18 is fused to non-conductive spacer 20 and non-conductive spacer 20 is fused to inner insulator 14 by heating the lead body. Fusing requires the heating of the various insulating layers to a point where contact between the layers will adhere the adjacent layers. To fuse the materials, a shrink-wrap, a vacuum or other method may be utilized. Using the shrink-wrap method, a shrink-wrap material is disposed about the outermost layer of insulating material. The entire assembly is then heated to shrink the shrink-wrap and soften the insulating material sufficiently to facilitate fusing of the inner insulating material with the outer insulating material or alternatively between the insulator layers and the non-conductive spacer. After heating, the assembly is typically allowed to cool before removal of the shrink-wrap material and removal of the mandrel. Using the vacuum method, a tube is disposed about the outermost layer of insulating material. With one end of the tube sealed and the other end of the tube attached to a vacuum pump, a partial vacuum is applied and the entire assembly is heated to soften the insulating material to facilitate fusing. After heating, the assembly is typically allowed to cool before removal of the tubing and removal of the mandrel.

After the formation of the lead body is performed, one or several electrodes are formed on the distal end of the lead body to enable the assembly to be used in a neurostimulation system. Various electrode attachment and/or formation techniques can be employed. One example of a preferred technique is disclosed in greater detail in U.S. patent application Ser. No. 11/074,572, filed Mar. 8, 2005, entitled "Method of Forming a Lead". As discussed in the '572 patent application, a welding region is formed in a lead body by exposing a respective conductor within the lead body, preferably using an excimer laser, without breaching an inner lumen (if present). The welding region may be in the form of a groove in the insulator. In alternative embodiments, the welding region may take a variety of forms and orientations that expose a sufficient surface area of the respective conductor to form an electrical connection with a conductive pad. When in the form of a groove, the welding region is typically formed such that the groove runs parallel to conductor (typically obliquely relatively to the lead body for helically wound conductors).

A conductive pad is then positioned within the welding region during manufacture to facilitate the electrical connection of a band electrode and the respective conductor. The conductive pad may be formed by centering a length of wire or other piece of material over the welding region and melting the wire or material at a point over the welding region. As the material melts, the ends of the wire are drawn into the welding region to form the conductive pad. A weld is typically used to secure the conductive pad in electrical contact with conductor. Alternatively, the conductive pad may be secured using an adhesive. The conductive pad may be composed of any of a variety of conductive materials that can be welded or secured with adhesives. Some suitable metals include stainless steel, MP35N, Pt—Ir, platinum, silver, gold, copper, vanadium or other metal that will be recognized by one skilled in the art upon review of this disclosure. The conductive pad is positioned within the welding region so that the conductive pad is in electrical contact with the conductor. Typically, the conductive pad is welded to the conductor prior to placing the band electrode over the welding regions and the conductive pad. A pulsed Neodymium:yttrium-arsenic-garnet (YAG) laser may be used to weld the conductive pad to the respective conductor.

A band electrode is placed over the lead body and welded to the respective conductive pad, thereby securing the band electrode to the lead body and electrically connecting the respective conductor and the band electrode. The band electrode may be further secured to the lead body by swaging, crimping and/or adhesives. Alternatively, the band electrode may be secured to the lead body by heating the lead body. Heating the lead body stress-relieves the plastic increasing the outside diameter and securing the band electrode over the lead body. In addition, heating the lead body may be used to create a lead having a uniform diameter between the band electrode and the lead body.

In some embodiments, electrical contacts can be formed on the proximal end of the lead body and coupled to conductors within the lead body in substantially the same manner as forming electrodes on the distal end (although a different technique could be used if desired). The electrical contacts facilitate electrical connection of the lead body to a pulse generator device (e.g., a neurostimulator). In alternative embodiments, the electrical contacts need not be formed. Instead, the lead body is used to connect to an "extension" lead which, in turn, is connected to the pulse generator device.

The invention claimed is:

1. A method for manufacturing a neurostimulation lead, comprising:
   providing a mandrel having inner insulating material disposed intermediate a first end and a second end of the mandrel, wherein the mandrel extends beyond the inner insulating material at the first end and the second end of the mandrel;
   securing respective first ends of a plurality of conductors to the first end of the mandrel;
   positioning the plurality of conductors spirally around the inner insulating material and securing respective second ends of the plurality of conductors to the second end of the mandrel;
   providing at least one insulating spacer;
   spirally winding the at least one insulating spacer between an adjacent pair of conductors of the plurality of conductors;
   disposing an outer insulating material around the wound plurality of conductors coextensive with the inner insulating material;
   fusing the inner insulating material, the at least one insulating space, and the outer insulating material to each other to form a lead assembly;
   forming a lead body from the lead assembly; and
   forming a stimulation lead, from the lead body, adapted for stimulation of neural tissue, the stimulation lead comprising at least one electrode.

2. A method, as in claim 1, wherein the fusing comprises:
   disposing shrink-wrap tubing over the outer insulating material; and
   heating the shrink-wrap, the outer insulating material, the at least one insulating spacer, and the inner insulating material to shrink the shrink-wrap tubing and fuse the outer insulating material, at least one insulating spacer, and the inner insulating material.

3. A method, as in claim 1, wherein the fusing comprises:
   disposing tubing over the outer insulating material;
   sealing a first end of the tubing;
   applying a partial vacuum to a second end of the tubing; and
   heating the tubing, wherein the partial vacuum draws the outer insulating material, the at least one insulating spacer, and the inner insulating material into contact and the heating fuses the outer insulating material, the at least one insulating spacer, and the inner insulating material thereby encapsulating the plurality of conductors.

4. A method, as in claim 1, further comprising:
   removing the mandrel from the inner insulator to form a lumen.

5. A method, as in claim 2, further comprising:
   removing the shrink-wrap material.

6. A method, as in claim 1, wherein the inner insulating material, the at least one insulating spacer, and the outer insulating material comprise material selected from the group consisting of polyurethane and silicone rubber.

7. A method of fabricating a lead for spinal neurological stimulation, comprising:
   providing a first insulator layer; spirally wrapping a plurality of conductors about the first insulator layer;
   spirally wrapping at least one insulating spacer about the first insulator layer in between at least two adjacent conductors of the plurality of conductors;
   providing a second insulator layer over the plurality of conductors and the at least one insulating spacer;
   fusing the first insulator layer, the at least one insulating spacer, and the second insulator layer to each other to form a lead body, wherein the plurality of conductors and the at least one insulating spacer extend substantially along the length of the lead body, the at least one spacer maintaining a pitch between the at least two adjacent conductors substantially along the length of the lead body; and
   forming a lead, from the lead body, for spinal neurological stimulation, the lead comprising a plurality of electrodes.

8. The method of claim 7 wherein the at least one insulating spacer is wrapped about the first insulator layer simultaneously with the wrapping of the plurality of conductors.

9. The method of claim 7 wherein the first insulator layer, the at least one insulating spacer, and the second insulator layer have similar melting points.

10. The method of claim 7 wherein the fusing comprising:
    applying heat to the first insulator layer, the at least one insulating spacer, and the second insulator layer to adhere the first insulator layer, the at least one insulating spacer, and the second insulator layer to each other without substantially disrupting their respective shapes.

* * * * *